(12) United States Patent
Bombardelli et al.

(10) Patent No.: US 6,767,916 B2
(45) Date of Patent: Jul. 27, 2004

(54) CHALCONE COUMARINS

(75) Inventors: Ezio Bombardelli, Milan (IT); Piero Valenti, Bologna (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/075,625

(22) Filed: Feb. 15, 2002

(65) Prior Publication Data

US 2002/0161036 A1 Oct. 31, 2002

Related U.S. Application Data

(63) Continuation of application No. PCT/EP00/08367, filed on Aug. 28, 2000.

(30) Foreign Application Priority Data

Sep. 3, 1999 (GB) ................................................ 9920908

(51) Int. Cl.[7] .................... C07D 405/10; A61K 31/4433
(52) U.S. Cl. ...................... 514/337; 546/283.1; 514/337
(58) Field of Search ........................ 546/283.1; 514/337

(56) References Cited

U.S. PATENT DOCUMENTS

| 5,525,625 A | 6/1996 | Bridges et al. ............. 514/456 |
| 5,808,137 A | 9/1998 | Bombardelli et al. ....... 560/255 |

FOREIGN PATENT DOCUMENTS

| FR | 2387956 | * 11/1978 | ......... C07D/213/04 |
| WO | WO 91/17749 | 11/1991 | |

OTHER PUBLICATIONS

Thaker et al, Synthesis of 2'-(3"-pyridyl)-y-pyranocoumarins and 3'-hydroxy-2'-(3"-pyridyl)-y-pyranocoumarins.*
CA 95:203793, Thakar et al. 1981.*
CA 92:58620, Fr. 2387956, 1980.*
Verma, A.K. et al,. "Inhibition of 7, 12–Dimethylbenz(α)anthracene– and N–Nitrosomethylurea–induced Rat Mammary Cancer by Dietary Flavonol Quercetin," Cancer Research 48, pp. 5754–5758, 1988.
Baird, W. et al., "Natural Products as a Source of Potential Cancer Chemotherapeutic and Chemopreventive Agents," Journal of Natural Products, 53;1, pp. 23–41, 1990.
Larocca, L.M. et al., "Type II Oestrogen Binding Sites in Acute Lymphoid and Myeloid Leukaemias: Growth Inhibitory Effect of Oestrogen and Flavonoids," British Journal of Hermatology, 75, pp. 489–495, 1990.

Scambia, G. et al., "Inhibitory Effect of Quercetin on OVCA 433 Cells and Presence of Type II Oestrogen Binding Sites in Primary Ovarian Tumours and Cultured Cells," Br. J. Cancer, 62, pp. 942–946, 1990.
Gogusev, J. et al., "Genotype Markers and Proto–Oncogene Analysis in the CD30–Positive "Malignant Histiocytosis," Del Cell Line With t(5;6)(q35;21),"" Int. J. Cancer, 46, pp. 106–112, 1990.
Scambia, G. et al., "Inhibitory Effect of Quercetin on Primary Ovarian and Endometrial Cancers and Synergistic Activity with cis–Diamminedichloroplatinum(II)," Gynecologic Oncology, 45, pp. 13–19, 1992.
Skehan, P. et al., "New Colorimetric Cytotoxicity Assay for Anticancer–Drug Screening," Journal of the National Cancer Institute, 82:13, pp. 1107–1112, 1990.
Sharan, P. et al., "Synthesis of some 7–Hydroxy–4–methylcoumarin–8–yl Chalcones and related Iso–oxazoles as Potential Fungicides," J. Indian Chem. Soc., 66, pp. 393–394, 1989.
Nair, M.S. et al., "Synthesis of Some Functionalized Oxapolyquinanes," Indian Journal of Chemistry, 27B, pp. 701–706, 1988.
Sangwan, N.K. et al., "Synthesis and Biological Properties of Substituted 2H–1–Benzopyran–2–ones and 2H, 10H–Benzo[1,2–b:3,4–b']dipyran–2, 10–diones," Journal f. prakt. Chemie., 330:1, pp. 137–141, 1988.

* cited by examiner

Primary Examiner—Ceila Chang
Assistant Examiner—Janet Coppins
(74) Attorney, Agent, or Firm—Jones Day

(57) ABSTRACT

Disclosed are novel chalcone derivatives having the formula (I).

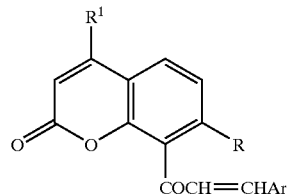

(I)

These compounds possess antiproliferative activity, and are useful for the manufacture of a medicament for the treatment or prevention of neoplasms, particularly those located in the uterus, ovary or breast. The compounds of the invention may also be useful in the manufacture of a medicament for the treatment or prevention of menopausal disorders and osteoporosis.

13 Claims, No Drawings

CHALCONE COUMARINS

This is a continuation of International Application no. PCT/EP00/08367, with an international filing date of Aug. 28, 2000, published in English under PCT article 21(2).

FIELD OF THE INVENTION

The invention relates to a novel class of compounds which have a structures related to naturally and synthetically occurring chalcones, as well as to methods for preparation of such compounds and to pharmaceutical uses thereof.

TECHNICAL FIELD

The compound 1,3-diphenyl-2-propene-1-one is known by the trivial name chalcone. Many naturally occurring flavanoids share structural features with chalcone and are referred to by the generic term "chalcones". Also certain flavanoids, including ones which are classified as chalcones, have recently been demonstrated to have anticancer activity (Cancer Research 48, 5754, 1988) and chemopreventive activity in some tumours (J. Nat. Prod. 53, 23, 1990).

In particular, quercetin, an ubiquitous flavonoid found in plants, has been shown to act on the proliferation of human leukemic cells (Br. J. of Haematology, 75, 489, 1990) and on other cell lines (Br. J. Cancer 62 94, 942, 1990; Int. J. Cancer, 46, 112, 1990; Gynaecologic Oncology, 45, 13, 1992) and to possess a synergic action with common antiblastic drugs.

In addition, some natural or synthetic chalcones, described in our International Patent Publication No. WO 9117749 and in International Patent Publication No. WO 96/19209 (Baylor College of Medicine) have proved to have a significant antiproliferation activity on a variety of different cell lines.

Although the mechanism of action of the antiproliferative activity of flavonoids and chalcones is still unknown, it is believed to be linked to the interaction of these compounds with type II estrogen receptors.

The action in vivo of these polyphenol substances is certainly much more complicated. All these compounds are generally characterised by an almost complete insolubility in water and, in vivo, by a very poor bioavailability linked to a rapid metabolism of phenols and a marked affinity for lipids and proteins.

Surprisingly, it has now been found that certain novel chalcones, chalcone derivatives and chalcone analogues, in particular ones in which the phenyl ring in the 1-position is substituted or replaced by rings containing one or more heteroatoms, possess a greater antiproliferation activity both on sensitive cancerous cells and on cells which are resistant to common chemotherapeutic drugs, including the latest generation anti-neoplastic agents, pacitaxel and docetaxel.

SUMMARY OF THE INVENTION

Thus according to one aspect of the present invention, there is provided a compound of Formula (I):

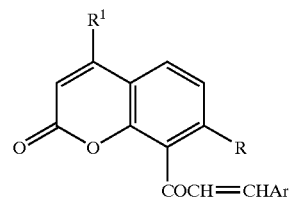

or a pharmaceutically acceptable salt or solvate thereof wherein:

Ar represents:
a substituted or unsubstituted, (preferably aromatic), carbocyclic or heterocyclic group, said carbocyclic or heterocyclic group containing from 5 to 10 ring atoms, said ring atoms forming one or two rings, wherein the or each ring contains 5 or 6 ring atoms, any heteroatoms being selected from N, O and S, any substituents on the Ar group being independently selected from the group consisting of:
(a) Cl, (b) Br, (c) F, (d) OH, (e) $NO_2$, (f) $CF_3$, (g) $C_{1-4}$ lower alkyl (in particular $CH_3$), (h) $SCH_3$, (i) $NHCOCH_3$, (j) $N(R^6)(R^8)$ wherein $R^6$ and $R^8$ are the same or different and each represents H or lower $C_{1-4}$ alkyl, (k) $OR^{10}$ wherein $R^{10}$ represents a saturated or unsaturated lower $C_{1-6}$ straight or branched hydrocarbyl group which may be unsubstituted or substituted by 1, 2 or 3 substituents selected from:

Cl, Br, F, OMe, $NO_2$ and $CF_3$, and (I) —$OCOR^{11}$, wherein $R^{11}$ represents a saturated or unsaturated lower $C_{1-6}$ straight or branched hydrocarbyl group or a phenyl group;

R represents
OH, $OR^{10}$ or $OCOR^{11}$, wherein $R^{10}$ and $R^{11}$ are as defined above; and $R^1$ represents H or a lower $C_{1-6}$ straight or branched hydrocarbyl group which may be unsubstituted or substituted by 1, 2 or 3 substituents selected from Cl, Br, F, OMe, $NO_2$ and $CF_3$.

DETAILED DESCRIPTION OF THE PREFERRED EMBODIMENTS

A preferred class of compounds of Formula (I) are those wherein Ar represents a substituted or unsubstituted (preferably aromatic), heterocycle group said heterocyclic group containing from 5 to 10 ring atoms, said ring atoms forming one or two rings, wherein the or each ring contains 5 or 6 ring atoms the heteroatoms being selected from N, O, and S , and any substituents on the Ar group being independently selected from the group consisting of:
a) Cl, (b) Br, (c) F, (d) OH, (e) $NO_2$, (f) $CF_3$, (g) $C_{1-4}$ lower alkyl (in particular $CH_3$), (h) $SCH_3$, (i) $NHCOCH_3$, (j) $N(R^6)(R^8)$ wherein $R^6$ and $R^8$ are the same or different and each represents H or lower $C_{1-4}$ alkyl (preferably $R^6$ and $R^8$ are the same or different and each represent H or lower $C_{1-4}$ alkyl), (k) $OR^{10}$ wherein $R^{10}$ represents a saturated or unsaturated lower $C_{1-6}$ straight or branched hydrocarbyl group which may be unsubstituted or substituted by 1, 2, or 3 substituents selected from:

Cl, Br, F, OMe, $NO_2$ and, $CF_3$, and (1) —OCOR$^{11}$ wherein R$^{11}$ represents a saturated or unsaturated lower C$_{1-6}$ straight or branched hydrocarbyl group or a phenyl group.

In a preferred class of compounds, Ar contains a basic nitrogen function, for example, by virtue of a heterocyclic nitrogen ring atom being present, or Ar may contain a substituent having a basic nitrogen, such as an amine, or an acetamido function. Thus accordingly, the Ar group is preferably a substituted or unsubstituted (preferably aromatic), heterocyclic group, said heterocyclic group containing from 5 to 10 ring atoms, wherein at least one of the ring atoms is a nitrogen atom and any substituent on the ring is as defined as for Formula (I). Particularly preferred Ar groups include pyridyl or indolyl.

A second preferred group of compounds of Formula (I) are those wherein Ar represents a substituted or unsubstituted (preferably aromatic), carbocyclic group, said carbocyclic group containing from 5 to 10 ring atoms, said ring atoms forming one or two rings, wherein the or each ring contains 5 or 6 ring atoms, and any substituents on the Ar group being independently selected from the group consisting of.

(a) Cl, (b) Br, (c) F, (d) OH, (e) NO$_2$, (f) CF$_3$, (g) C$_{1-4}$ lower alkyl (in particular CH$_3$), (h) SCH$_3$, (i) NHCOCH$_3$, (j) N(R$^6$)(R$^8$) wherein R$^6$ and R$^8$ are the same or different and each represents H or lower C$_{1-4}$ alkyl, (k) OR$^{10}$ wherein R$^{10}$ represents a saturated or unsaturated lower C$_{1-6}$ straight or branched hydrocarbyl group which may be unsubstituted or substituted by 1, 2 or 3 substituents selected from:

Cl, Br, F, OMe, NO$_2$ and CF$_3$, and (I) —OCOR$^{11}$, wherein R$^{11}$ represents a saturated or unsaturated lower C$_{1-6}$ straight or branched hydrocarbyl group or a phenyl group.

For the compounds of Formula (I), any substituents on the Ar group are preferably selected from the group consisting of: NHCOCH$_3$, N(R$^6$)(R$^8$), OR$^{10}$ and —COR$^{11}$, wherein R$^6$, R$^8$, R$^{10}$ and R$^{11}$ are as defined as above for Formula (I). R$^{10}$ and R$^{11}$ preferably represent a saturated or unsaturated C$_{1-6}$ straight chain or branched hydrocarbyl group, in particular methyl, ethyl, n-propyl or isopropyl.

Of this preferred class, Ar is preferably substituted with one or more OR$^{10}$ groups, wherein R$^{10}$ represents a saturated or unsaturated lower C$_{1-6}$ straight or branched hydrocarbyl group. An especially preferred R$^{10}$ group is methyl. Particularly preferred Ar groups include phenyl or phenyl substituted with 1, 2 or 3 methoxy groups.

For the preferred class of compounds wherein Ar comprises at least one basic nitrogen function, and wherein Ar represents a carbocyclic ring, the basic nitrogen function is provided by virtue of the carbocyclic ring comprising at least one substituent selected from NHCOCH$_3$ or N(R$^6$)(R$^8$), wherein R$^6$ and R$^8$ are as defined as for Formula (I).

For the compounds of Formula (I), R preferably represents an unsaturated lower C$_{1-6}$ straight or branched hydrocarbyl group. In particular, R represents OCH=C(CH$_3$)$_2$, OCH$_2$CMe=CH$_2$, OCH$_2$CH=CH$_2$ or OCH$_2$C≡CH. An especially preferred group of compounds are those wherein Ar is selected from phenyl, trimethoxyphenyl, 3-pyridyl, 4-pyridyl or 3-indolyl and R is selected from OCH=C(CH$_3$)$_2$, OCH$_2$CMe=CH$_2$, OCH$_2$CH=CH$_2$ or OCH$_2$C≡CH.

For the compounds of Formula (I), R$^1$ preferably represents a lower C$_{1-6}$ straight or branched hydrocarbyl group, especially methyl.

A further group of preferred compounds of Formula (I) include those wherein:

Ar represents
 phenyl, which may be unsubstituted or substituted by one, two or three substituents independently selected from Cl, Br, F, OMe, NO$_2$, CF$_3$, C$_{1-4}$ lower alkyl (in particular CH$_3$), NMe$_2$, NEt$_2$, SCH$_3$ and NHCOCH$_3$;
 thienyl, 2-furyl, 3-pyridyl, 4-pyridyl or indolyl.
R represents
 OH or OCH$_2$R$^1$, wherein R$^1$ is selected from —CH=CMe$_2$, —CMe=CH$_2$, —CH=CH$_2$ and —C≡CH.

It will be appreciated that compounds of Formula (I) which contain a basic amino function may be converted to acid addition salts, with pharmacologically acceptable acids, e.g. hydrochloric acid and phosphoric acid. Such salts are also included in the present invention.

The present invention also provides the use of a compound of Formula (I) in the manufacture of an antiproliferative medicament In particular, the compounds of the present invention may be useful for the manufacture of a medicament for the treatment or prevention of neoplasms, particularly those located in the uterus, ovary or breast. In particular, the compounds may be useful for the manufacture of a medicament for the treatment of cancer cells that are resistant to paclitaxel and docetaxel.

The compounds of Formula (I) may advantageously be used in combination therapies involving the combined use of a compound of Formula (I) and another anti-neoplastic agent, especially paclitaxel or docetaxel. The combination therapy may involve simultaneous or successive administration of a compound of Formula (I) and an anti-neoplastic agent. Such combination therapy forms a further aspect of the invention.

The compounds of the invention may be further used in the manufacture of a medicament for the treatment or prevention of menopausal disorders and osteoporosis.

The present invention further includes a pharmaceutical composition comprising one of more of the compounds of Formula (I) in combination with one or more pharmaceutically acceptable excipients.

The invention will now be described by way of illustrative examples and with reference to the accompanying formulae drawings.

EXAMPLES

Example 1

General Conditions to Obtain Chalcones

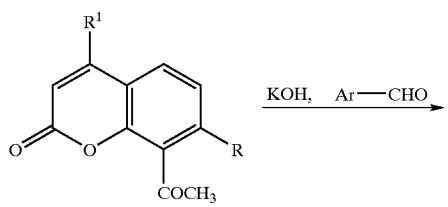

-continued

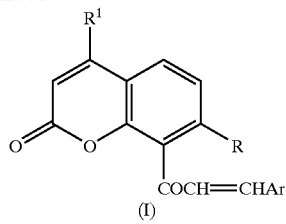
(I)

Method A.

A solution of KOH 50% (3 ml) is added to an equimolar solution of a ketone (0.0075 mol) and an aldehyde (0.0075 mol) in ethanol 95%; the addition is performed under energetic stirring at room temperature. The reaction is left under stirring for one night and then diluted with water and acidified. The precipitate is separated by filtration and dried under vacuum. The compounds are crystallized by ethanol or first separated by chromatography and then crystallized by ethanol.

Method B.

A solution of a ketone (0.0075 mol), an aldehyde (0.0075 mol), piperidine (15 ml) and acetic acid (75 ml) in ethyl alcohol 95% (80 ml) is countercurrent heated for 5 hours. Molecular sieves are added to the solution to eliminate water and the whole is left at rest for one night. The precipitate that is generally obtained is gathered and crystallized. If the product does not precipitate in these conditions, the solvent is vacuum evaporated and the residue is purified by chromatography on silica gel column.

Example 2

1-[4-Methyl-7-(2-methylprop-1-enyloxy)coumarin-8-yl]-3-(pyridine-3-yl)-propen-1-one (See Accompanying Formula Drawing VIB 106).

A solution of KOH 50% (3 ml) is added to an equimolar solution of 4-methyl-7-(3-methylbut-2-enyloxy)-8-acetylcoumarin (2.14 g, 0.0075 mol) and pyridin-3-carboxy aldehyde (0.8 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by ethanol to give 0.84 g of product m.p. 156–157° C., $^1$H-NMR (CDCl$_3$)δ: 1.69 (s, 3H); 1.72 (s, 3H); 2.44 (d, 3H, J=1.22 Hz); 4.65 (d, 2H, J=6.5 Hz); 5.34–5.38 (m, 1H); 6.16 (d, 1 H, J=1.2 Hz); 6.95 (d, 1H=J 8.8 Hz); 7.07 (d, 1 H, J=18 Hz); 7.36 (d, 1 H); 7.30–7.40 (m, 1 H); 7.64 (d, 1 H, J=8.9 Hz); 7.90 (m, 1 H); 8.58–8.68 (m, 2H).

Example 3

1-[4-Methyl-7-(3-methylbut-2-enyloxy)coumarin-8-yl]-3-phenyl-propen-1-one (See Accompanying Formula Drawing VIB 119)

A solution of KOH 50% (3 ml) is added to an equimolar solution of 4-methyl-7-(3-methylbut-2-enyloxy)-8-acetylcoumarin (2.14 g, 0.0075 mol) and benzaldehyde (0.8 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by ethanol to give 1.34 g of product m.p. 114–16° C., $^1$H-NMR (CDCl$_3$) δ: 1.69 (s, 3H); 1.72 (s, 3H); 2.44 (d, 3H, J=1.22 Hz); 4.65 (d, 2H, J=6.5 Hz); 5.34–5.38 (m, 1H); 6.16 (d, 1H, J=1.2 Hz); 6.95 (d, 1H, J=8.8 Hz); 7.00 (d, 1H, J=18 Hz); 7.10 (d, 1H); 7.30–7.40 (m, 3H); 7.45–7.52 (m, 12H); 7.61 (d, 1H, J=8.9 Hz).

Example 4

1-[4-Methyl-7-(3-methylbut-2enyloxy)coumarin-8-yl]-3-(3,4,5-tri-methoxyphenyl)propen-1-one (See Accompanying Formula Drawing VIB 120)

A solution of KOH 50% (3 ml) is added to an equimolar solution of 4-methyl-7-(3-methylbut-2-enyloxy)-8-acetylcoumarin (2.14 g, 0.0075 mol) and 3,4,5-trimethoxy-benzaldehyde (1.47 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by methanol to give 1.3 g of product m.p. 148–150° C., $^1$H-NMR (CDCl$_3$) δ: 1.69 (s, 3H,); 1.72 (s, 3H); 2.44 (d, 3H, J=1.2 Hz); 3.74–3.88 (m, 9H); 4.65 (d, 2H, J=6.5 Hz); 5.34–5.38 (m, 1H); 6.16 (s, 1H); 6.93 (d, 1H, J=16 Hz); 6.95 (d, 1H, J=8.9 Hz); 7.25 (d, 1H, J=16 Hz); 7.63 (d, 1H, J=8.9 Hz).

Example 5

1-[4-Methyl-7-(2-methylallyloxy)coumarin8-yl]-3-(pyridine-3-yl)propen-1-one (See Accompanying Formula Drawing VIB 122)

A solution of KOH 50% (3 ml) is added to an equimolar solution of 4-methyl-7-methylallyloxy-8-acetylcoumarin (2.04 g, 0.0075 mol) and pyridin-3-carboxy-aldehyde (0.8 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by methanol to give 0.8 g of product m.p. 110–12° C., $^1$H-NMR (CDCl$_3$) δ: 1.74 (s, 3H); 2.43 (s, 3H); 4.55 (s, 2H); 4.98 (d, 2H, J=15 Hz); 6,16 (s, 1H); 6.93 (d, 1H, J=8.9 Hz); 7.09 (d, 1H, J=16 Hz); 7.35–7.37 (m, 1H); 7.36 (d, 1H, J=16 Hz); 7.64 (d, 1H, J=8.9 Hz); 7.85 (d, 1H, J=7 Hz); 8.58 (d, 1H, J=5 Hz); 8.67 (s, 1H).

Example 6

1-[4-Methyl-7-(2-methylallyloxy)coumarin-8-yl]-3-phenyl-propen-1-one (See Accompanying Formula Drawing VIB 121)

A solution of KOH 50% (3 ml) is added to an equimolar solution of 4-methyl-7-methylallyloxy-8-acetylcoumarin (2.04 g, 0.0075 mol) and benzaldehyde (0.8 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by methanol to give 1.2 g of product m.p. 158–160° C., $^1$H-NMR (CDCl$_3$) δ: 1.74 (s, 3H); 2.43 (s, 3H); 4.55 (s, 2H); 4.98 (d, 2H, J=15 Hz); 6,16 (s, 1H); 6.93 (d, 1H, J=8;9 Hz); 7.02 (d, 1H, J=16 Hz); 7.43–7.53 (m, 4H); 7.61 (d, 1H, J=8.9 Hz).

Example 7

1-[4Methyl-7-(2-methylallyloxy)coumarin-8-yl]-3-(3-methoxyphenyl)-propen-1-one (See Accompanying Formula Drawing VIB 162)

A solution of KOH 50% (3 ml) is added to an equimolar solution of 4-methyl-7-methylallyloxy-8-acetylcoumarin (2.04 g, 0.0075 mol) and 3-methoxybenzaldehyde (1.01 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by methanol to give 1.6 g of product m.p. 85–87° C., $^1$H-NMR (CDCl$_3$) δ: 1.74 (s, 3H); 2.43 (s, 3H); 3.85–3.88 (m, 3H); 4.55 (s, 2H); 4.98 (d, 2H, J=15 Hz); 6,16 (s, 1H); 6.93 (d, 1H, J=8.9 Hz); 7.02 (d, 1H, J=16 Hz); 6.95–7.12 (m, 3H); 7.26 (m, 1H); 7.30 (d, 1H, J=16 Hz); –7.61 (d, 1H, J=8.9 Hz).

Example 8

1-[4-Methyl-7-(2-methylallyloxy)coumarin-8-yl]-3-(3,4,5-trimethoxy-phenyl)-propen-1-one (See Accompanying Formula Drawing VIB 123)

A solution of KOH 50% (3 ml) is added to an equimolar solution of 4-methyl-7-methylallyloxy-8-acetylcoumarin (2.04 g, 0.0075 mol) and 3,4,5-trimethoxy-benzaldehyde (1.47 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by methanol to give 1.7 g of product m.p. 128–130° C., $^1$H-NMR (CDCl$_3$) δ: 1.74 (s, 3H); 2.43 (s, 3H); 3.75–3.88 (m, 9H); 4.55 (s, 2H); 4.98 (d, 2H, J=15 Hz); 6,16 (s, 1H); 6.72 (s, 1H); 6.93 (d, 1H, J=8.9 Hz); 6.94 (d, 1H, J=16 Hz); 7.23 (d, 1H, J=16 Hz); 7.61 (d, 1H, J=8.9 Hz).

Example 9

1-[4-Methyl-7-(allyloxy)coumarin-8-yl]-3-phenyl-propen-1-one (See Accompanying Formula Drawing VIB 158)

A solution of KOH 50% (3 ml) is added to an equimolar solution of 4-methyl-7-allyloxy-8-acetylcoumarin (1.93 g, 0.0075 mol) and benzaldehyde (0.8 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by methanol to give 1.1 g of product m.p. 136–139° C., $^1$H-NMR (CDCl$_3$) δ: 2.43 (s, 3H); 4.65 (d, 2H, J=5.1 Hz); 4.25–4.55 (m, 2H); 5.15–5.35 (m, 1H); 6,16 (s, 1H); 6.93 (d, 1H, J=8.9 Hz); 7.03 (d, 1H) J=16 Hz); 7.04–7.15 (m, 3H); 7.15–7.26 (m, 1H); 7.33 (d, 1H, J=16 Hz); 7.64 (d, 1H, J=8.9 Hz).

Example 10

1-[4-Methyl-7-(allyloxy)coumarin-8-yl]-3-(pyridin-3-yl)-propen-1-one (See Accompanying Formula Drawing VIB 161)

A solution of KOH 50% (3 ml) is added to an equimolar solution of 4methyl-7-allyloxy-8-acetylcoumarin (1.93 g, 0.0075 mol) and pyridin-3-carboxyaldehyde (0.8 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by ethanol to give 0.6 g of product m.p. 124–126° C., $^1$H-NMR (CDCl$_3$) δ: 2.43 (s, 3H); 4.65 (d, 2H, J=5.1 Hz); 4.25–4.55 (m, 2H); 5.15–5.35 (m, 1H); 6.16 (s, 1H); 6.93 (d, 1H, J=8.9 Hz); 7.08 (d, 1H, J=16 Hz); 7.30 (d, 1H, J=16 Hz); 7.49 (d, 1H, J=8.9 Hz); 7.83–7.87 (m, 1H); 8.58 (d, 1H, J=5 Hz); 6.87 (s, 1H).

Example 11

1-[4-Methyl-7-(allyloxy)coumarin-8-yl]-3-(3-methoxyphenyl)-prop n-1-one (See Accompanying Formula Drawing VIB 159).

A solution of KOH 50% (3 ml) is added to an equimolar solution of 4-methyl-7-allyloxy-8-acetylcoumarin (1.93 g, 0.0075 mol) and 3-methoxybenzaldehyde (1.01 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by methanol to give 1.6 g of product m.p. 61–63° C. $^1$H-NMR (CDCl$_3$) δ: 2.43 (s, 3H); 3.82 (s, 3H); 4.65 (d, 2H, J=5.1 Hz); 5.20–5.42 (m, 2H); 5.82–6.02 (m, 1H); 6,16 (s, 1H); 6.90 (d, 1H, J=8,9 Hz); 7.15 (d, 1H, J=16 Hz); 6.90–7.15 (m, 3H); 7.15 (d, 1H, J=16 Hz); 7.20–7.29 (m, $_1$H); 7.30 (d, 1H, J=16 Hz); 7.64 (d, $_1$H, J=8.9 Hz).

Example 12

1-[4-Methyl-7-(allyloxy)coumarin-3-yl]-3-(3,4,5-trimethoxyphenyl)-propen-1-one (See Accompanying Formula Drawing VIB 160)

A solution of KOH 50% (3 ml) is added to an equimolar solution of 4-methyl-7-allyloxy-8-acetylcoumarin (1.93 g, 0.0075 mol) and 3-methoxybenzaldehyde (1.47 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by methanol to give 1.8 g of product m.p. 138–140° C. $^1$H-NMR (CDCl$_3$) δ: 2.43 (s, 3H); 3.82–3.91 (m, 9H); 4.65 (d, 2H, J=5.1 Hz); 5.25–5.40 (m, 2H); 5.90–6.02 (m, 1H); 6.16 (s, 1H); 6.74 (s, 2H); 6.90–7.15 (m, 3H); 7.15 (d, 1H, J=16 Hz); 7.20–7.29 (d, 1H, J=16 Hz); 7.70 (d, 1H, J=8.9).

Example 13

1-[4-Methyl-7-(prop-2-ynyloxy)coumarin-8-yl]-3-(3,4,5-trimethoxy-phenyl)-propen-1-one (See Accompanying Formula Drawing VIB 126)

A solution of KOH 50% (3 ml) is added to an equimolar solution of 4-methyl-7-prop-2-ynyloxy-8-acetylcoumarin (1.92 g, 0.0075 mol) and 3,4,5-trimethoxy-benzaldehyde (1.47 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by ethanol to give 1.1 of product m.p. 191–93° C., $^1$H-NMR (CDCl$_3$) δ: 2.45 (s, 3H); 2.53–2.56 (m, 1H); 3.83–3.85 (m, 9H); 4.82 (d, 2H, J=2.2 Hz); 6.20 (s, 1H); 6.72 (s, 2H); 6.92 (d, 1H, J=16 Hz); 7.12 (d, 1H, J=8.9 Hz); 7.15 (d, 1H, J=16 Hz); 7.67 (d, 1H, J=8.9 Hz).

Example 14

1-[4-Methyl-7-(prop-2-ynyloxy)coumarin-8-yl]-3-phenylpropen-1-one (See Accompanying Formula Drawing VIB 124)

A solution of KOH 50% (3 ml) is added to an equimolar solution of 4-methyl-7-prop-2-ynyloxy-8-acetylcoumarin (1.92 g, 0.0075 mol) and benzaldehyde (0.8 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by ethanol to give 0.8 g of product m.p. 140–42° C., $^1$H-NMR (CDCl$_3$) δ: 2.45 (s, 3H); 2.53–2.56 (m, 1H); 4.82 (d, 2H, J=2.2 Hz); 6.20 (s, 1H); 7.02 (d, 1H, J=16 Hz); 7;13 (d, 1H, J–=8.9 Hz); 7.32 (d, 1H, J=16 Hz); 7.35–7.45 (m, 3H); 7.48–7.52 (m, 2H); 7.67 (d, 1H, J=8.9 Hz).

Example 15

1-[4-Methyl-7-(prop-2-ynyloxy)coumarin-8-yl]-3-(pyridin-3-yl)-propen-1-one (See accompanying Formula Drawing VIB 125)

A solution of KOH 50% (3 ml) is added to an equimolar solution of 4-methyl-7-prop-2-ynyloxy-8-acetylcoumarin (1.92 g, 0.0075 mol) and pyridin-3-carboxy aldehyde (0.8 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by ethanol to give 0.7 g of product m.p. 203–205° C., $^1$H-NMR (CDCl$_3$) δ: 2.45 (s, 3H); 2.53–2.56 (m, 1H); 4.82 (d 2H, J=2.2 Hz); 6.20 (s, 1H); 7.02 (d, 1H, J=16 Hz); 7.13 (d, 1H, J=8.9 Hz); 7.32 (d, 1H, J=16 Hz); 7.28–7.35 (m, 1H); 7.69 (d, 1H, J=8.9 Hz); 7.88–7.92 (m, 1H); 8.58–8.62 (m, 1H); 8.66 (s, 1H).

Example 16

1-[4-Methyl-7-(prop-2-ynyloxy)coumarin-8-yl]-3-(3-methoxyphenyl)-propen-1-one (See Accompanying Formula Drawing VIB 163)

A solution of KOH 50% (3 ml) is added to an equimolar solution of 4-methyl-7-prop2-ynyloxy-8-acetylcoumarin (1.92 g, 0.0075 mol) and 3-methoxybenzaldehyde (1.01 g, 0.0075 mol) in ethanol 95%; the addition is performed under energetic stirring at room temperature. The reaction is left under stirring for one night and then diluted with water and acidified. The precipitate is separated by filtration and dried under vacuum. The compound is crystallized by methanol to give 1.5 g of product m.p. 154–56° C., $^1$H-NMR (CDCl$_3$) δ: 2.45 (s, 3H); 3.48 (m, 1H; 3.81 (s, 3H); 4.82 (d, 2H, J=2.2 Hz); 6.15 (s, 1H); 6.90–7.26 (m, 5H); 7.10 (d, 1H, J=8.9 Hz); 7.65 (d, 1H, J=8.9 Hz).

Example 17

1-[4-Methyl-7-(allyloxy)coumarin-8-yl]-3-(4-chlorophenyl)-propen-1-one (See Accompanying Formula Drawing VIB 241)

A solution of KOH 50% (3 ml) is added to an equimolar solution of 4-methyl-7-allyloxy-8-acetylcoumarin (1.93 g, 0.0075 mol) and 4-chlorobenzaldehyde (1.05 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 1.1 g of product m.p. 153–155° C., $^1$H-NMR (CDCl$_3$) δ: 2.42 (d, J=1.2 Hz, 3H), 4.65 (m, 2H), 5.2 (m, 2H), 6.15 (m, 1H), 6.91–7.61 (m, 8H).

Example 18

1-[4-Methyl-7-(prop-2ynyloxy)coumarin-8-yl]-3-(4-fluoro-phenyl)-propen-1-one (See Accompanying Formula Drawing VIB 240)

A solution of KOH 50% (3 ml) is added to an equimolar solution of 4-methyl-7-prop2-ynyloxy-8-acetylcoumarin (1.92 g, 0.0075 mol) and 4-fluorobenzaldehyde (0.93 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by ethanol to give 1.2 g of product m.p. 185–186° C., $^1$H-NMR (CDCl$_3$) δ: 2.43 (d, J=1.2 Hz, 3H), 2.52 (m, 1H), 4.79 (d, J=1.2 Hz, 2H), 6.17 (d, J=1.2 Hz, 1H), 6.96–7.66 (m, 8H).

Example 19

1-[3-methyl-7-methoxy)coumarin-8-yl]-3-(2thienyl)-propen-1-one (See Accompanying Formula Drawing VIB 242)

A solution of KOH 50% (3 ml) is added to an equimolar solution of 7-methoxy-8-acetyl-3-methylcoumarine (1.74 g, 0.0075 mol) and 2-thio-phenecarboxyaldehyde (0.84 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 1.8 g of product m.p. 172–173° C., $^1$H-NMR (CDCl$_3$) δ: 2.46 (d, 3H), 4.0 (s, 3H), 6.21 (d, J=1.2 Hz, 1H), 6.91–7.84 (m, 7H).

Example 20

1-[4-Methyl-7-allyloxy)coumarin-8-yl]-3-(2,6dichloro-phenyl)-propen-1-one (See Accompanying Formula Drawing VIB 243)

A solution of KOH 50% (3 ml) is added to an equimolar solution of 4-methyl-7-allyloxy-8-acetylcoumarin (1.93 g, 0.0075 mol) and 2,6-dichlorobenzaldehyde (1.31 ág, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 1.1 g of product m.p. 149–151° C., $^1$H-NMR (CDCl$_3$) δ: 2.41 (m, 3H), 4.66 (m, 2H), 5.3 (m, 2H), 5.9 (m, 1H), 6.9–7.64 (m, 8H).

Biological Evaluation

Compounds VIB 106 and VIB 122 were tested for their cytotoxicity against drug-resistant cancer cells, both alone, and in combination with paclitaxel. The results of these studies are shown below.

When tested alone, compounds VIB 106 and VIB 122 were found to possess relatively low cytotoxicity (IC$_{50}$>1 μM) against drug-resistant cancer cells.

The compounds were then evaluated in combination with paclitaxel for their cytostatic activity against the drug-resistant breast cancer cells MDA435/LCC6-MDR. In the experiments, the compounds were used in combination with paclitaxel, the paclitaxel being at a concentration of 0.1 μM, the IC$_{50}$ of paclitaxel decreases by 3–5 fold when used in combination with each of compounds VIB 106 and VIB 122, i.e. from 426 nM to 130–86 nM compared with paclitaxel alone. Consequently, in the presence of these compounds, paclitaxel can recover its excellent inhibitory activities against the drug-resistant cancer cells.

TABLE 1

| Compound | IC$_{50}$/nM | % Reduction in IC$_{50}$ of paclitaxel |
|---|---|---|
| Paclitaxel | 426 | — |
| VIB 106 + Paclitaxel | 86 | 80 |
| VIB 122 + Paclitaxel | 130 | 70 |

Experimental

The treatment consisted of concurrent exposure of MDA-435/LCC-MDR cells to paclitaxel in the presence or absence of the compounds reversing agent (1 μM) for 72 h in vitro. Assessment of cytotoxicity, i.e. cell growth inhibition, was determined according to the methods of Skehan, et al. as discussed in J. Nat. Cancer Inst., 82, 1107,1990. Briefly, cells were plated between 400 and 1200 cells/well in 96 well plates and incubated at 37° C. for 15–18 h prior to drug addiction to allow attachment of cells. Compounds were solubilized in 100% DMSO and further diluted in RPMI-1640 containing 10 mM HEPES. After a 72 h incubation, 100 μl of ice-cold 50% TCA was added to each well and incubated for 1 h at 4° C. Plates were then washed 5 times with tap water to remove TCA, low-molecular weight metabolites and serum proteins. Sulforhodamine B (SRB) (0.4%, 50 μl) was added to each well. Following a five minute incubation at room temperature, plates were rinsed 5 times with 0.1% acetic acid and air dried. Bound dye was solubilized with 10 mM Tris Base (pH 10.5) for 5 min on a gyratory shaker. Optical density was measured at 570 nm.

VIB 106

VIB 119

VIB 120

VIB 122

VIB 121
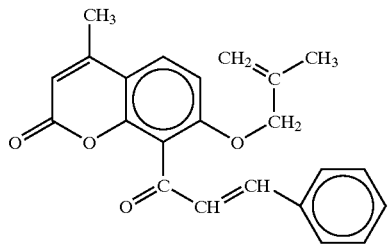

VIB 162
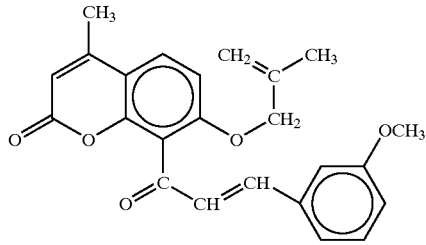

VIB 123
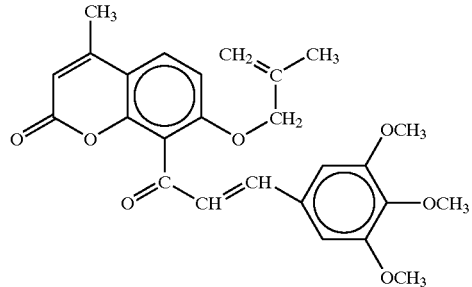

VIB 158
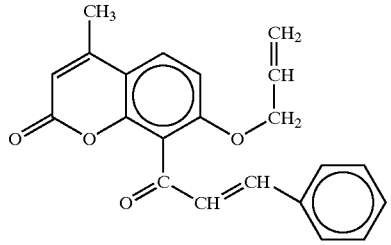

VIB 159
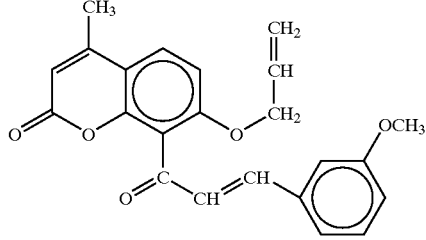

VIB 160
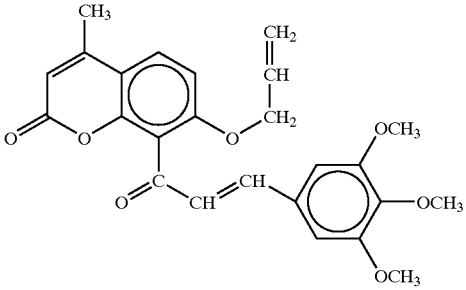

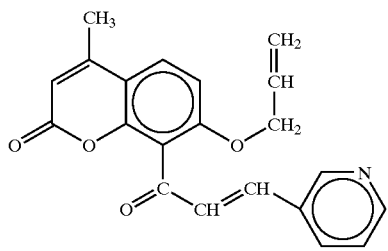
VIB 161

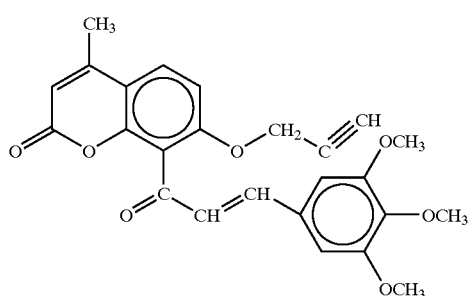
VIB 126

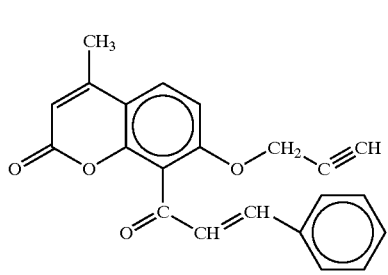
VIB 124

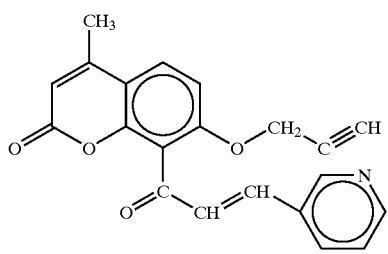
VIB 125

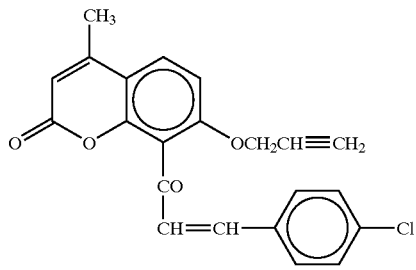
VIB 241

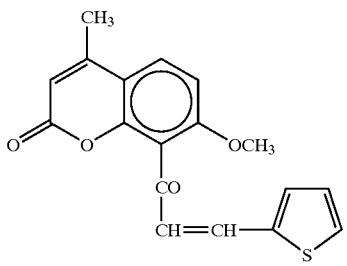
VIB 242

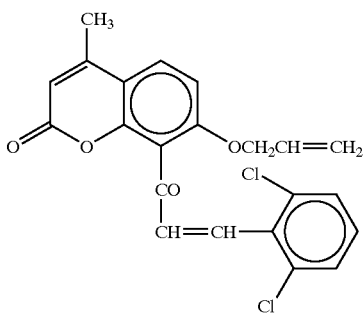
VIB 243

VIB 163

VIB 240

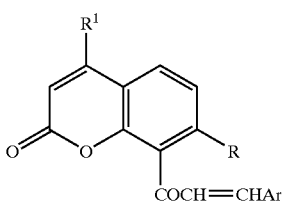

What is claimed is:

1. A compound of Formula (I):

$$\text{(I)}$$

or a pharmaceutically acceptable salt or solvate thereof wherein:

Ar represents: pyridyl which may be unsubstituted or substituted with one or more substituents selected from the group consisting of: (a) Cl, (b) Br, (c) F, (d) OH, (e) $NO_2$, (f) $CF_3$, (g) $C_{1-4}$ alkyl, (h) $SCH_3$, (i) $NHCOCH_3$, (j) $N(R^6)(R^8)$ wherein $R^6$ and $R^8$ are the same or different and each represents H or $C_{1-4}$ alkyl, (k) $OR^{10}$ wherein $R^{10}$ represent a saturated or unsaturated $C_{1-6}$ straight or branched hydrocarbyl group which may be unsubstituted or substituted with from 1 to 3 substituents selected from Cl, Br, F, OMe, $NO_2$ and $CF_3$, and (l) $-OCOR^{11}$ wherein $R^{11}$ represents a saturated or unsaturated $C_{1-6}$ straight or branched hydrocarbyl group or a phenyl group;

R represents OH, $OR^{10}$ or $OCOR^{11}$ wherein $R^{10}$ and $R^{11}$ are as defined above; and $R^1$ represents H or a $C_{1-6}$ straight or branched hydrocarbyl group which may be unsubstituted or substituted with from 1 to 3 substituents selected from Cl, Br, F, OMe, $NO_2$ and $CF_3$;

with the proviso that when $R^1$ is $CH_3$ and R is OH, then Ar cannot be 3-pyridyl or 4-pyridyl.

2. The compound of claim 1, wherein the substituents on the Ar group are selected from the group consisting of: $NHCOCH_3$, $N(R^6)(R^8)$, $OR^{10}$, and $-OCOR^{11}$.

3. The compound of claim 1, wherein Ar is substituted with one or more $OR^{10}$ groups and $R^{10}$ is a saturated or unsaturated $C_{1-6}$ straight or branched hydrocarbyl group.

4. The compound of claim 3, wherein $R^{10}$ is methyl.

5. The compound of claim 1, wherein $R^{10}$ is an unsaturated $C_{1-6}$ straight or branched hydrocarbyl group.

6. The compound of claim 5, wherein R is $OCH=C(CH_3)_2$, $OCH_2CMe=CH_2$, $OCH_2CH=CH_2$, or $OCH_2C\equiv CH$.

7. The compound of claim 1, wherein Ar is selected from 3-pyridyl, and 4-pyridyl; and R is selected from $OCH=C(CH_3)_2$, $OCH_2CMe=CH_2$, $OCH_2CH=CH_2$ or $OCH_2C\equiv CH$.

8. The compound of claim 1, wherein Ar is selected from 3-pyridyl and 4-pyridyl and R is selected from OH, $OCH=C(CH_3)_2$, $OCH_2CH=C(CH_3)_2$, $OCH_2C(CH_3)=CH_2$, $OCH_2CH=CH_2$, and $OCH_2C\equiv CH$.

9. The compound of claim 1, wherein $R^6$ and $R^8$ are the same or different and each is independently H or $C_{1-4}$ alkyl.

10. The compound of claim 1, wherein $R^{10}$ and $R^{11}$ are each independently a saturated or unsaturated $C_{1-6}$ straight chain or branched hydrocarbyl group.

11. The compound of claim 10, wherein $R^{10}$ and $R^{11}$ are selected from methyl, ethyl, n-propyl, and isopropyl.

12. The compound of claim 1, selected from the group consisting of:

- 1-[4-methyl-7-(2-methylprop-1-enyloxy)coumarin-8-yl]-3-(pyridine-3-y)propen-1-one;
- 1-[4-methyl-7-(2-methylallyloxy)coumarin-8-yl]-3-(pyridine-3-yl)propen-1-one;
- 1-[4-methyl-7-(allyloxy)coumarin-8-yl]-3-(pyridin-3-yl)propen-1-one; and
- 1-[4-methyl-7-(prop-2-ynyloxy)coumarin-8-yl]-3-(pyridin-3-yl)propen-1-one.

13. A pharmaceutical composition comprising a compound of claim 1 and a pharmaceutically acceptable excipient.

* * * * *